United States Patent
Quiroz et al.

(10) Patent No.: US 9,974,301 B2
(45) Date of Patent: May 22, 2018

(54) **FUNGICIDAL COMPOSITION FOR CONTROLLING PHYTOPATHOGENIC DISEASES, COMPRISING A MIXTURE OF THE VOLATILE COMPOUNDS ETHANOL, 3-METHYLBUTANOL, ISOBUTYL ACETATE, ISOAMYL ACETATE AND ALPHA-BISABOLOL; AND THE USE THEREOF FOR INHIBITING THE GROWTH OF THE PATHOGENIC FUNGUS *BOTRYTIS CINEREA***

(71) Applicant: UNIVERSIDAD DE LA FRONTERA, Temuco (CL)

(72) Inventors: Andres Quiroz, Temuco (CL); Heidi Schalchli, Temuco (CL); Emilio Hormazabal, Temuco (CL)

(73) Assignee: UNIVERSIDAD DE LA FRONTERA, Temuco (CL)

( * ) Notice: Subject to any disclaimer, the term of this patent is extended or adjusted under 35 U.S.C. 154(b) by 0 days. days.

(21) Appl. No.: 15/108,993

(22) PCT Filed: Dec. 31, 2013

(86) PCT No.: PCT/IB2013/061449
§ 371 (c)(1),
(2) Date: Jun. 29, 2016

(87) PCT Pub. No.: WO2015/101809
PCT Pub. Date: Jul. 9, 2015

(65) Prior Publication Data
US 2016/0330957 A1    Nov. 17, 2016

(51) Int. Cl.
*A01N 37/02*    (2006.01)
*A01N 31/02*    (2006.01)
*A01N 31/04*    (2006.01)
*A01N 63/04*    (2006.01)

(52) U.S. Cl.
CPC .............. *A01N 37/02* (2013.01); *A01N 31/02* (2013.01); *A01N 31/04* (2013.01); *A01N 63/04* (2013.01)

(58) Field of Classification Search
None
See application file for complete search history.

(56) References Cited

U.S. PATENT DOCUMENTS

2010/0255124 A1    10/2010    Green et al.
2010/0272690 A1*   10/2010    Gandhi

FOREIGN PATENT DOCUMENTS

| ES | 2366856 A1 | 10/2011 |
| MX | 2011011397 A | 2/2012 |
| WO | 2012123605 A1 | 9/2012 |

OTHER PUBLICATIONS

Tabanca et al., "Chemical Composition and Antifungal Activity of Arnica longifolia, Aster hesperius, and Chrysothamnus nauseosus Essential Oils", Journal of Agricultural and Food Chemistry, 2007, vol. 55, pp. 8430-8435.*
H. Schalchli, et al; Antifungal activity of ovolatile metabolites emitted by mycelial cultures of . . . ; Chemistry and ecology; vol. 27; No. 6; 2011; pp. 503-513.
International Search Report dated Jul. 1, 2014 for PCT/IB2013/061449 and English translation.

* cited by examiner

*Primary Examiner* — Savitha M Rao
*Assistant Examiner* — Gregg Polansky
(74) *Attorney, Agent, or Firm* — Lucas & Mercanti, LLP

(57) ABSTRACT

This invention relates to a fungicidal composition for controlling phytopathogenic diseases, comprising a mixture of volatile compounds: 14-17% v/v ethanol, 28-33% v/v 3-methylbutanol, 18-21% v/v isobutyl acetate, 17-20% v/v isoamyl acetate, and 13-16% v/v alpha-bisabolol, relative to the total volume of the composition. The invention also relates to the use of the fungicidal composition in order to inhibit the growth of the pathogenic fungus *Botrytis cinerea*.

2 Claims, 3 Drawing Sheets

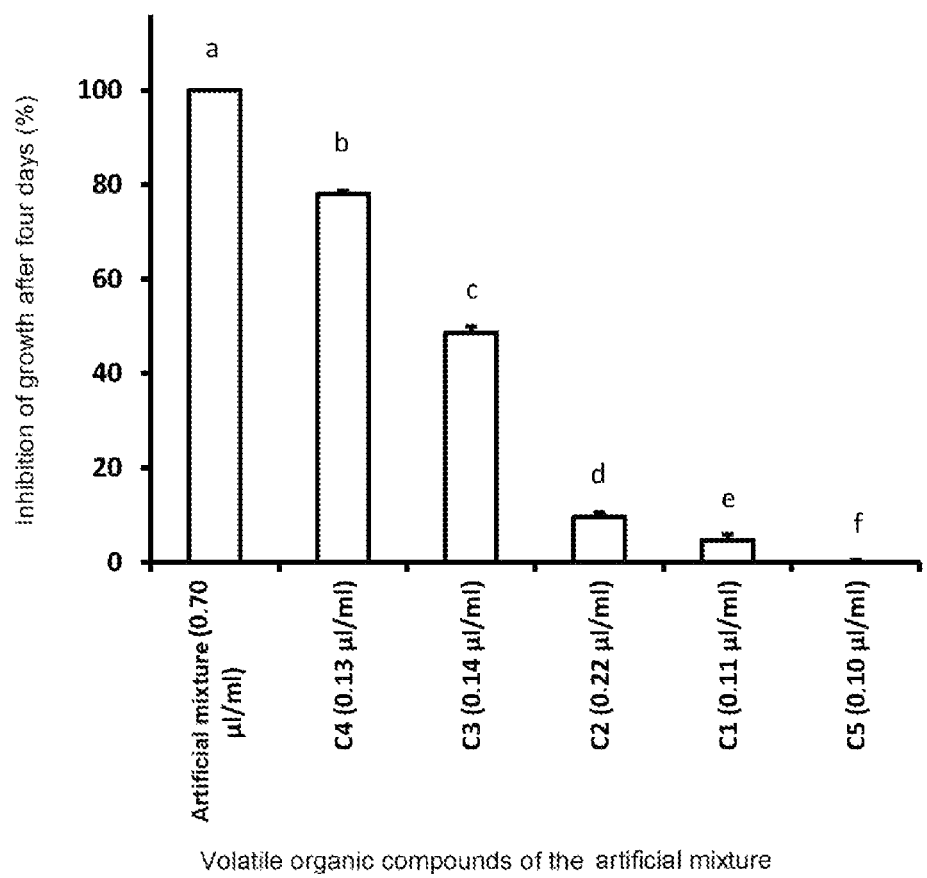

FUNGICIDAL COMPOSITION FOR CONTROLLING PHYTOPATHOGENIC DISEASES, COMPRISING A MIXTURE OF THE VOLATILE COMPOUNDS ETHANOL, 3-METHYLBUTANOL, ISOBUTYL ACETATE, ISOAMYL ACETATE AND ALPHA-BISABOLOL; AND THE USE THEREOF FOR INHIBITING THE GROWTH OF THE PATHOGENIC FUNGUS *BOTRYTIS CINEREA*

CROSS REFERENCE TO RELATED APPLICATION

This Application is a 371 of PCT/IB2013/061449 filed on Dec. 31, 2013 which is incorporated herein by reference.

FIELD OF THE INVENTION

The present invention falls in the field of fungicides for biological control of pest, and in particular, is directed to a fungicidal composition comprising a mixture of synthetic or natural compounds, or mixture of both, for controlling phytopathogenic diseases. In particular, the composition of the present invention is useful for the control of pathogen *Botrytis cinerea*.

STATE OF THE ART

*Botrytis cinerea* is a pathogenic fungus of many vegetal species, animals and bacteria, although its most economically important host is the grapevine. In viticulture is commonly known as *Botrytis* rot while in horticulture affects many other plants.

*B. cinerea*, commonly known as gray mold is a disease that does not have a specific host, but strongly attacks economically important fruits, such as berries (blueberries, strawberries, strawberries, etc.) and the aforementioned grapevine. Symptoms vary depending on the type and part of the plant being attacked. However, in berries and grapevine fruits, it is shown as a fine woven gray (mycelium), which give rise to spores, which constitute the mode of spreading the disease, which occurs when plants or fruits are subjected to some kind of movement. This disease overwinters on dead tissue. The fruits attacked by this fungus rot.

Thus, in horticulture, the impact of the disease caused by *Botrytis cinerea* is also economically important in soft fruits such as strawberries. Unlike grapes, affected strawberries are not edible and are discarded. It is recommended to optimize ventilation to minimize infection under field conditions and prevent moisture being trapped between leaves and fruit. The above measure is accompanied with a slight raising of the strawberry plants from ground using straw, rather than directly planting on the ground, where the effect of moisture is more direct.

Currently, the control of pathogen *B. cinerea* in berries species is based on the use of chemical fungicides, such as captan, thiram or benomyl. The main problem arising from the use of chemical fungicides is the increase of genetic resistance of *B. cinerea* to fungicides. In addition to the strict exportation rules in force for berries and fruits in general, regulating the use of these synthetic chemicals. For example, the pesticide benomyl [IUPAC name: methyl 1-(butylcarbamoyl)benzimidazol-2-ylcarbamate] can interfere with hormone metabolism, and its use has been restricted by environmental and health reasons.

Furthermore, the prior art shows the study of biological control of *B. cinerea* through the use of *Trichoderma* strains. Notwithstanding this, the control agents from *Trichoderma* strains are not yet commercially applied on crops and/or postharvest products.

In addition, the closest prior art discloses in the scientific article "*Antifungal activity of volatile metabolites emitted by mycelial cultures of saprophytic fungi*", 2011, the identification of the antifungal molecular activity of *Trichoderma viride, Schizophyllum commune* and *Trametes versicolor* on pathogen fungi *Botrytis cinerea, Fusarium oxysporum* and *M. miehei*, the document discloses that among the studied saprophytes fungi, only an isolated *S. commune* showed the highest inhibitory activity against *B. cinerea* and *M. miehei* ($86.0 \pm 5.4$ and $99.5 \pm 0.5\%$, respectively). The volatile profiles of isolates contained different classes of compounds, where the major components detected were 6-pentyl-$\alpha$-pyrone (in *T viride*), ethanol and $\beta$-bisabolol (in *S. commune*), and a sesquiterpene alcohol (in *Tr. versicolor*).

Besides the scientific article "*Volatile antimicrobials from Muscodor albus, a novel endophytic fungus*", 2001, discloses that another fungus *Muscodor albus* effectively inhibits and kills other fungi and bacteria through a mixture of volatile organic compounds produced by this fungus. The document discloses that each of the classes of volatile organic compounds produced by the fungus (alcohols, esters, ketones, acids and lipids) has some inhibitory effect against the tested fungus or bacteria, but none of them was lethal.

However, the prior art gives no indication that a mixture, defined in each of its components consisting of natural compounds from fungi or artificially obtained synthetic compounds, or mixture of both, could have a demonstrated fungicidal effect on *B. cinerea* where the pathogenic fungus would be completely eliminated (100% inhibition).

SOLUTION TO THE TECHNICAL PROBLEM

The composition of the present invention corresponds to a mixture of organic compounds of volatile features ("*Volatile Organic Compounds*" or VOCs, for its acronym in English), which are naturally released by a cosmopolitan saprophytic fungus. The composition may also comprise those VOCs where the compounds have a synthetic origin. Due to its bioactivity and long distance action mechanism, the volatile organic compounds constitute a real alternative to using chemicals that have been known for increasing the genetic resistance to fungicide, the accumulation of toxins in food and the contamination of environment.

In this regard, the present invention provides a fungicidal composition comprising a mixture of synthetic or natural compounds, or mixtures thereof, for controlling phytopathogenic diseases. In particular, the composition of the present invention is especially useful for controlling pathogen *Botrytis cinerea*.

DESCRIPTION OF FIGURES

FIG. 3 shows a graph of the percent of inhibition after four days (%±SD) of *Botrytis cinerea* growth exposed to the artificial mixture and to each one of the five (C1-C5) pure Volatile Organic Compounds emitted by *Schizophyllum commune* forming said mixture. C1 corresponds to ethanol, C2 corresponds to 3-methylbutanol, C3 corresponds to isobutyl acetate, C4 corresponds to isoamyl acetate and C5 corresponds to α-bisabolol. Equal letters indicate that there is no significant difference according to the Kruskal-Wallis test ($P>0.05$).

DESCRIPTION OF THE INVENTION

Figure 1:
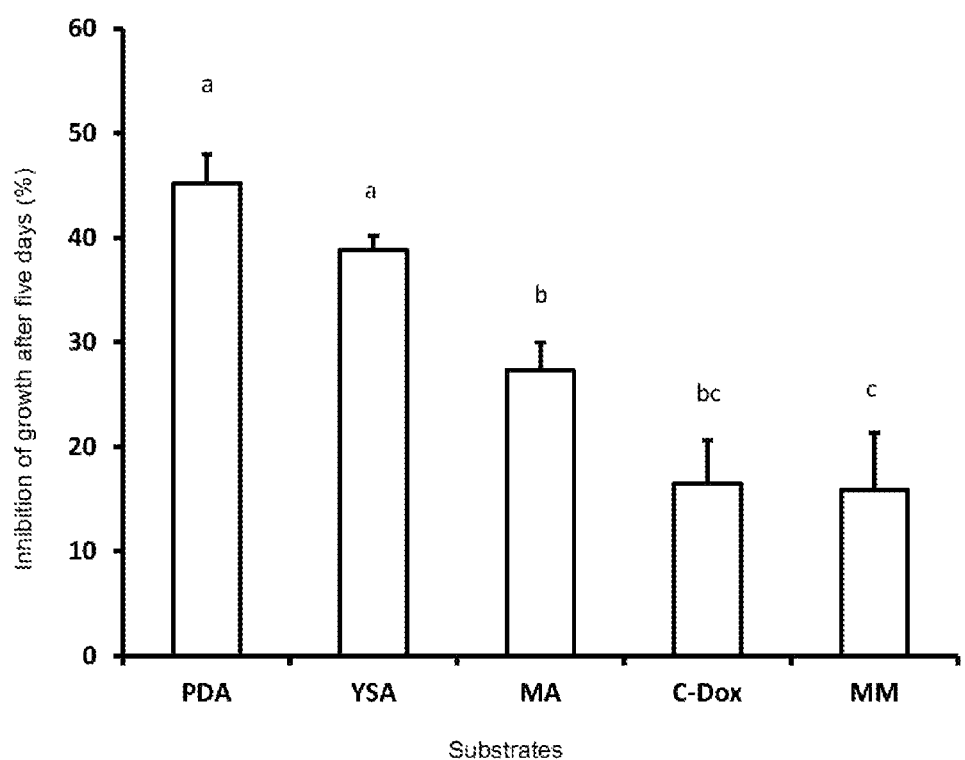
FIG. 1 shows a graph of average growth inhibition after 5 days (%±SD) of *Botrytis cinerea* exposed to volatiles released from *Schizophyllum commune*, grown on different substrates at 25° C.±1. PDA corresponds to potato dextrose agar, YSA corresponds to yeast extract sucrose agar, MA corresponds to malt extract agar, C-Doc corresponds to Czapek-Dox, and MM corresponds to minimal medium. Different letters indicate the existence of significant differences according to Tukey test ($\alpha=0.05$).

The present invention provides a fungicidal composition comprising a mixture of synthetic or natural compounds, or mixtures thereof, for controlling phytopathogenic diseases such as gray mold caused by *Botrytis cinerea*.

For the purposes of the present invention, the composition corresponds to a mixture artificially created, or artificial mixture, which can be effectively used to inhibit the growth of the pathogenic fungus *Botrytis cinerea* in a 100%, after a period of time of at least 2 days, at least 3 days, or after 4 days.

The composition corresponds to a mixture of volatile organic compounds from *Schizophyllum commune* or volatile synthetic compounds artificially obtained, and consists of ethanol, 3-methylbutanol, isobutyl acetate, isoamyl acetate and alpha-bisabolol, at a concentration ranging between 0.5 and 0.9 µl/mL. It is preferred that the composition of the invention comprises between 14 and 17% v/v ethanol, between 28 to 33% v/v 3-methylbutanol; between 18 and 21% v/v isobutyl acetate; between 17% to 20% v/v isoamyl acetate; and between 13 and 16% v/v alpha-bisabolol, relative to the total volume of the composition.

In a further preferred embodiment, the present invention consists of between 15.5-16.5% v/v ethanol; between 31-32% v/v 3-methylbutanol; between 19.5-20.5% v/v isobutyl acetate; between 18-19% v/v isoamyl acetate; 13.5-14.5% v/v alpha-bisabolol, relative to the total volume of the composition.

While the composition of the invention comprises a mixture of volatile compounds; all compounds are in liquid state, where a value of µl [in µl/mL] corresponds to the pure compound volume in the liquid state, or in case of the mixture, the sum of the volumes of compounds in liquid state in a mixing ratio given by its natural release. While a value of mL [in µl/mL], stands for the head space volume in the assays, which is air. In other words, the latter corresponds to the volume of air wherein compound vapors are diffused. In this context, it is preferred that the final mixture in the composition has a concentration of 0.5-0.9 µl/mL, this means 0.5-0.9 µl of mixture per 1 ml of air volume in the head space where the compounds are diffused, or more preferably at a concentration ranging between 0.6 and 0.8 µl/mL, this means 0.6-0.8 µl of mixture per 1 ml of air volume in the head space where the compounds are diffused. In particular, the composition of the present invention is particularly useful for controlling the pathogen *Botrytis cinerea*, which may be present in more than 200 different vegetal species, such as fruits, vegetables and flowers.

For example, to obtain the composition of the invention was required to entrap and characterize each of the volatile organic compounds naturally produced by *Schizophyllum commune*, grown under different growth conditions. Alternatively, each of the compounds in the composition was artificially obtained from synthetic compounds. Furthermore, the composition may comprise a mixture of both, naturally produced compounds together with synthetic compounds.

Once determined the growth condition in which the pathogenic fungus *Botrytis* is inhibited with a greater inhibition power or potency (i.e.: condition where the highest inhibition % is observed), each of the compounds and its relative or proportional concentration in that condition are identified. The mixture of the invention was calculated according to the relative percentage of each of the compounds that are naturally emitted by the saprophytic fungus *S. commune*.

Finally, the inhibition of *Botrytis* by the mixture of the invention is assayed, demonstrating the effectiveness of said mixture which is capable of inhibiting 100% of the pathogenic fungus growth in 4 days.

It is also estimated that the lethal dose of the mixture is in the range of 0.70 µl/mL while the minimum inhibitory concentration is in the range of 0.30 µl/mL.

The detailed procedure to produce or formulate the fungicidal composition comprising the volatile compound mixture of the invention is detailed below.

Obtaining Fungi

The saprophytic fungus *Schizophyllum commune* Fr. (Genbank accession number JF694037) was collected from a native forest located in the South Central area of Chile (latitude, 38° 39' South; longitude 72° 35' West). *Botrytis cinerea* Pers.:Fr. (teleomorph: *Botryotinia fuckeliana* (de Bary) Whetzel) was obtained from the strain collection of the Institute of Agricultural Research (INIA-Quillamapu, Chile). Both fungi were grown in potato dextrose agar (PDA, Difco Laboratories, Detroit, Mich., USA) on dishes at 25° C. in the dark for a week.

Antifungal Activity of Saprophytic Fungus

In a first step, the inhibitory activity of volatiles emitted by *S. commune* was verified. For this, bi compartmentalized Petri dishes (94×16 mm) (Greiner, Germany) coated with culture medium were used, leaving a head space of 60 mL. One compartment was inoculated with mycelium (3 mm radius disk) of the saprophytic fungus (*S. commune*). The other compartment was inoculated with fresh mycelium of *B. cinerea*. In this bioassay there was no physical contact between the two fungi. The control treatment consisted of placing the mycelium of *B. cinerea* in only one of the compartments. All experimental units (Petri dishes) were covered and sealed with Parafilm M®, and incubated at 25° C. in the dark until the growth of any fungi (treatment and control) reached the edge of the central wall of the Petri dish. The mycelial growth was measured using a magnifying glass (Japan Optical), and data were expressed as percent of inhibition relative to control. Each treatment was repeated 10 times.

Once the inhibitory activity was tested (see FIG. 1), the volatile organic compounds were trapped in order to be identified.

Entrapment of Volatile Organic Compounds.

Volatile organic compounds emitted by the fungus *S. commune* were trapped by Solid Phase Micro Extraction (SPME). Within a 40 mL vial of SPME (Supelco, Inc., Pa., USA) was deposited a disc of 3 mm radius of fresh mycelium of *S. commune* with different culture media and incubated between 5 and 8 days at 25° C.±1° C. in the dark. The volatiles were adsorbed on a 65 µm polydimethylsiloxane/divinylbenzene (PDMS/DVB) fiber for 30 minutes at 25° C. Controls only consisted in vials containing each of the different culture media. Volatile Organic Compounds emitted by the fungus once adsorbed, were desorb from the fiber. For this, the fiber was introduced into the gas chromatograph injection chamber which was at a temperature of 250° C.

Analysis by Gas Chromatography-Mass Spectrometry

This analysis was conducted using a gas chromatograph (Model Focus, Thermo Electron Corporation, Waltham, USA) coupled to a mass spectrometer (Model DSQ, Thermo Electron Corporation) equipped with a capillary column BP-1 (30 m, 0.2 mm, 0.33 μm). The carrier gas was Helium at a flow of 1.5 mL min$^{-1}$. Mass spectra were acquired from 35 to 500 a.m.u. (atomic mass units). Sample ionization was by electron impact at 70 eV and 200° C. in the ion source. SPME fiber was inserted into the GC injector for thermal desorption in splitless mode for 2 minutes, the injector temperature was maintained at 250° C. The GC oven temperature was programmed to rise from 40° C. to 260° C. at 5° C. min$^{-1}$ and then maintained for 5 minutes. Compounds were identified by means of: a) comparison with mass spectra from a mass spectra library, b) comparison with mass spectra of commercial standards (Sigma-Aldrich, Germany).

Figure 2:
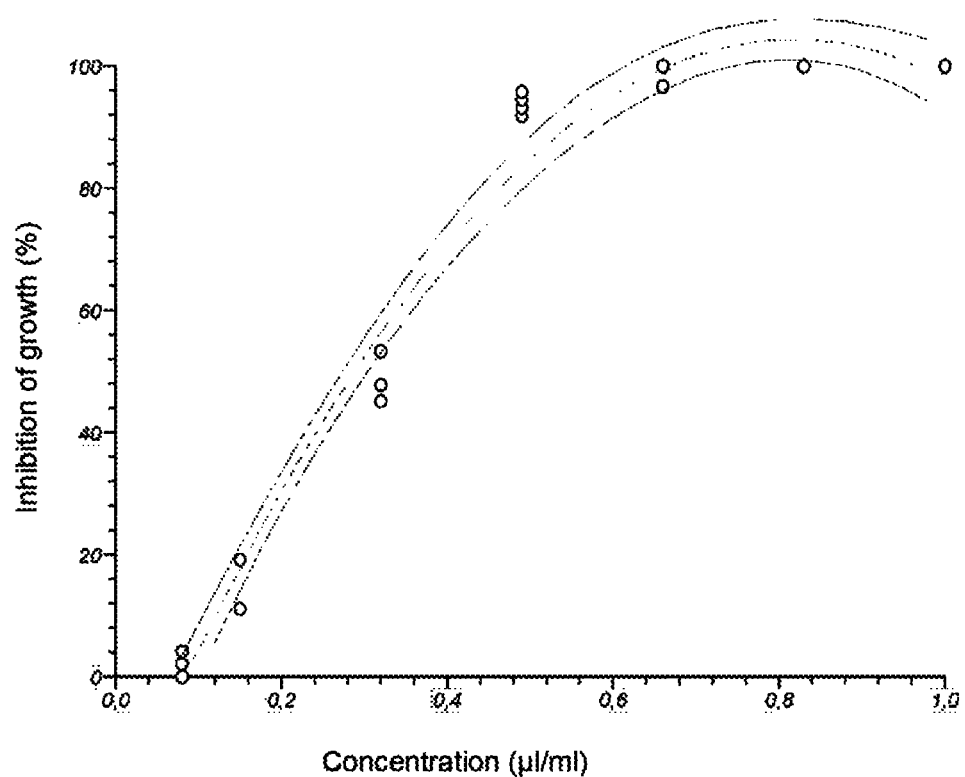
FIG. 2 shows a graph of the polynomial regression of the percent of growth inhibition of *Botrytis cinerea* exposed to a mixture of volatiles emitted by *Schizophyllum commune*, grown on potato dextrose agar (PDA).

Table 1 below, shows the compounds released by *S. commune* in different culture media. Data in Table 1 correspond to assays where a 65 μm polydimethylsiloxane/divinylbenzene (PDMS/DVB) fiber was used to collect the Volatile Organic Compounds released by saprophytic fungus. All volatiles were identified by comparing mass spectra with data of NIST MS Search 2.0 library. The same letters indicate that there is no significant difference between the substrates according to the Kruskal-Wallis test ($P>0.05$) followed by a Conover-Inman test.

was similar to that detailed above to assess the antifungal activity of saprophytic fungus. The minimum inhibitory concentration (MIC) and lethal dose 50% ($LD_{50}$) were calculated by interpolation according to the polynomial equation ($Y=-194.565812 \times 2+318.001954 \times -25.561441$; $r2=0.982$) (See FIG. 2). Statistically calculated MIC and $LD_{50}$ values were 0.67 and 0.29 μl/mL. MIC was then experimentally adjusted to 0.70 μl/mL. Meanwhile, each of the five pure compounds in the mixture were tested at different concentrations according to their relative proportions obtained according to the MIC values calculated for the artificial mixture (0.70 μl/mL).

Thus, a mixture of the 5 components released by *S. commune*, such as ethanol, 3-methyl-butanol, isobutyl acetate, isoamyl acetate and α-bisabolol was used. These compounds are commercially available and were purchased from Aldrich Company with a purity greater than 99%. The percentage of each of the components in the mixture was calculated according to their natural release from fungus *S. commune* grown on PDA, which was the combination with a greater inhibition power (about 45%, as seen in FIG. 1) over *B. cinerea*. Thus, the mixture was formed as follows:

Ethanol=15.71%
3-methyl-butanol=31.43%
Isobutyl acetate=20.00%
Isoamyl acetate=18.57%
α-bisabolol=14.29%

TABLE 1

Volatile Organic Compounds emitted by *Schizophyllum commune* grown under different culture media.

| Retention Time (minutes) | Chemical Name | Volatiles compounds captured on different substrates (Relative Area % ± SD) | | | | |
|---|---|---|---|---|---|---|
| | | potato dextrose agar (PDA) | malt extract agar (MA) | yeast extract sucrose agar (YSA) | minimal medium (MM) | Czapek-Dox (C-Dox) |
| 1.18 | Ethanol* (C1) | 19.5 ± 0.7a | — | 9.6 ± 1.3a | — | — |
| 1.65 | Ethyl Acetate | — | — | 8.5 ± 2.3a | — | — |
| 2.21 | S-Methyl ethanothiocyanate | — | — | 31.2 ± 1.9a | — | — |
| 2.65 | 3-Methylbutanol* (C2) | 39.2 ± 4.22a | 9.7 ± 4.1b | 1.3 ± 0.4c | — | — |
| 2.72 | 2-Methylbutanol | — | — | 5.8 ± 0.7a | — | — |
| 2.97 | Ethyl isobutyrate | — | — | 1.4 ± 0.4a | — | — |
| 3.15 | Isobutyl acetate* (C3) | 24.4 ± 20.4ab | 44.2 ± 15.3a | 12.7 ± 1.4b | — | — |
| 3.57 | Ethyl butanoate | — | — | 1.2 ± 0.3a | — | — |
| 4.52 | Ethyl 2-methylbutyrate | — | — | 5.1 ± 1.5a | — | — |
| 5.05 | Isoamyl acetate* (C4) | 23.0 ± 3.8a | 9.0 ± 2.8b | 1.5 ± 0.3c | — | — |
| 5.15 | 2-Methylbutyl acetate | — | 37.1 ± 22.1a | 21.3 ± 4.9a | — | — |
| 7.02 | Dimethyl trisulfure | — | — | 0.4 ± 0.2a | — | — |
| 21.58 | β-Himachalene | — | — | — | — | — |
| 25.71 | α-Bisabolol (C5) | 17.4 ± 13.0a | — | — | — | — |

APPLICATION EXAMPLE

Inhibition of growth of phytopathogenic fungus *Botrytis cinerea* by an artificial mixture of VOCs at laboratory level.

Volatiles emitted by *S. commune* grown with PDA culture medium were selected for this bioassay, because this strain in this medium caused a significantly more inhibition of the growth of *Botrytis*. Selected compounds are those marked with an asterisk (*) in Table 1.

The inhibitory power of pure compounds and of a mixture based on their percent ratio were assessed. The methodology 6 formulations were tested at laboratory level:

Formulation 1: 0.70 μl of the artificial mixture per 1 mL of head space volume (airspace).

Formulation 2: 0.11 μl ethanol per 1 mL of head space volume (airspace).

Formulation 3: 0.14 μl of isobutyl acetate per 1 mL of head space volume (airspace).

Formulation 4: 0.13 μl of isoamyl acetate per 1 mL of head space volume (airspace).

Formulation 5: 0.10 μl of α-bisabolol per 1 mL of head space volume (airspace).

The effect of each formulation for inhibiting the growth of *B. cinerea* was tested using bi compartmentalized dishes, according to the above methodology. FIG. 3 shows the antifungal activity of the artificial mixture and the pure compounds towards *B. cinerea*. From the results is seen that the artificial mixture inhibited 100% of growth, isoamyl acetate 77% and isobutyl acetate 47%. In contrast, α-bisabolol did not inhibit the growth of *B. cinerea*, while ethanol and 3-methyl-butanol did it between 5 and 10%

The results obtained in the laboratory allow us to conclude that the use of a composition comprising the artificial mixture formed by 5 particular volatile compounds achieve the complete removal of the pathogenic fungus *B. cinerea*.

The invention claimed is:

1. A fungicidal composition for controlling phytopathogenic diseases, comprising a mixture of volatile compounds entrapped from *Schizophyllum commune*, the mixture comprising:
   between 14 and 17% v/v ethanol,
   between 28 to 33% v/v 3-methylbutanol,
   between 18 and 21% v/v isobutyl acetate,
   between 17% to 20% v/v isoamyl acetate and
   between 13 and 16% v/v alpha-bisabolol, relative to the total volume of the composition.

2. The fungicidal composition according to claim 1, wherein
   ethanol is between 15.5-16.5% v/v;
   3-methylbutanol is between 31-32% v/v;
   isobutyl acetate is between 19.5-20.5% v/v;
   isoamyl acetate is between 18-19% v/v;
   alpha-bisabolol is 13.5-14.5% v/v, relative to the total volume of the composition.

* * * * *